(12) United States Patent
Sinha

(10) Patent No.: US 6,568,250 B1
(45) Date of Patent: May 27, 2003

(54) APPARATUS AND METHOD FOR DETERMINING RESIDUAL STRESS

(75) Inventor: Arvind K. Sinha, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/668,781

(22) Filed: Sep. 22, 2000

(51) Int. Cl.[7] .............................................. G01N 3/48
(52) U.S. Cl. ........................... 73/81; 702/33; 702/43
(58) Field of Search .............................. 703/81; 702/33, 702/42, 43

(56) References Cited

U.S. PATENT DOCUMENTS

| | | | | |
|---|---|---|---|---|
| 3,763,697 A | * | 10/1973 | Sturm | 73/88 R |
| 3,969,928 A | * | 7/1976 | Zarka | 73/88 R |
| 4,701,224 A | * | 10/1987 | Zado | 148/23 |
| 4,896,339 A | * | 1/1990 | Fukumoto | 377/19 |
| 5,146,779 A | * | 9/1992 | Sugimoto et al. | 73/81 |
| 5,382,757 A | * | 1/1995 | Ishida | 174/262 |
| 5,463,896 A | * | 11/1995 | Abbate et al. | 73/81 |
| 5,999,887 A | * | 12/1999 | Giannakopoulos et al. | 702/33 |
| 6,076,411 A | * | 6/2000 | Horvath | 73/866 |
| 6,134,954 A | * | 10/2000 | Suresh et al. | 73/81 |
| 6,155,104 A | * | 12/2000 | Suresh et al. | 73/81 |
| 6,311,135 B1 | * | 10/2001 | Suresh et al. | 702/43 |

OTHER PUBLICATIONS

"SwissRock 180 Universal Rockwell Hardness Tester", http://www.qualitest-inc.com/swissrock180.htm.

* cited by examiner

*Primary Examiner*—Helen Kwok
*Assistant Examiner*—C D Garber
(74) *Attorney, Agent, or Firm*—Martin & Associates, LLP

(57) ABSTRACT

An apparatus measures residual stress in a sample under test by measuring the penetration of an indenter on a unprocessed sample under test, and after processing of the sample under test, measuring again the penetration of the indenter on the processed sample under test, and deriving from the two penetration measurements the residual stress in a sample under test. The apparatus and method of the preferred embodiments are especially useful in determining residual stress in a printed wiring board. In this manner a direct measurement of residual stress is possible without destroying the printed wiring board.

9 Claims, 6 Drawing Sheets

APPARATUS AND METHOD FOR DETERMINING RESIDUAL STRESS

BACKGROUND OF THE INVENTION

1. Technical Field

This invention generally relates to test equipment and more specifically relates to equipment for testing properties of materials.

2. Background Art

Electronics have become essential to our modern way of life in the United States. Electronic assemblies are typically made by installing individual components into a printed wiring board (PWB), which are then soldered into place. The PWB makes all the connections between electronic and electrical components using metal paths that are typically etched into the PWB. Modern PWBs have become very sophisticated and complex, and it is not uncommon to have a PWB today that has in excess of twenty layers. Each layer defines conductor paths that connect to one or more other layers. The many different layers allow packing the components very tightly onto a PWB, thereby reducing the overall area of the PWB. This minimization in size of an electronic assembly is essential for many applications where the size of the electronic assembly must be kept very small, as in mobile phones and other hand-held electronic devices.

The reliability of an electronic assembly is directly related to the reliability of the PWB. The reliability of a PWB depends on the stresses that the PWB has undergone. While a PWB undergoes stresses while it is being manufactured, the stresses of particular interest are the stresses to the PWB after it is manufactured that occur during processing of the electronic assembly that includes the PWB. After a multi-layer PWB is made, it undergoes numerous processing steps. For example, the components are first incorporated into the PWB. High capacity operations use robots to place the components in their proper location on the PWB. The repeated pressure of placing the components on the PWB stresses the PWB. The soldering of the components also stresses the PWB. An electronic assembly typically undergoes burn-in testing at relatively-high temperatures to catch any parts that suffer from early failures. Burn-in testing causes more stress in the PWB. In addition, many electronic assemblies are tested across a temperature span for several cycles, which causes more stress in the PWB. For some electronic assemblies, the stresses induced into the PWB by the manufacturing process can significantly shorten the life of the electronic assembly. For this reason, testing for residual stress in PWBs has become the focus of increased attention in recent years.

Various methods have been proposed to measure residual stress in a printed wiring board. Non-destructive tests have been developed, which include X-ray analysis and neutron diffraction. However, these methods are not in widespread use for measuring residual stress in PWBs because they are not sufficiently accurate and are not well adapted to a high volume manufacturing environment. Other destructive tests have been developed that more accurately indicate the residual stress in a PWB, but these tests result in the destruction of the PWB. One example of destructive testing drills a hole in the PWB after placing strain gages on the PWB in proximity to the hole that allow measuring the strain before the hole is drilled and after the hole is drilled, and deriving from the changes in strain the residual stress of the board. The theory behind the hold drilling approach is that drilling the hole creates room for the PWB to "relax", thereby-relieving stress in that location. Another destructive test flexes a PWB that has not undergone manufacturing processes until it fails (i.e., cracks or breaks), the repeats the test on a PWB that has undergone manufacturing processes. By comparing the force required to break the PWB both before and after manufacturing processes, an estimate of residual stress can be derived, but this test again results in the destruction of the PWB. With some modern PWBs, such as motherboards in sophisticated computer systems, the expense of, the PWB is significant, and periodically destroying the boards to test for residual stress is not an acceptable solution. Without a way to accurately measure residual stress in a PWB without destroying the PWB, either the expense of testing for residual stress will continue to be excessive, or PWBs will not be adequately tested for residual stress.

DISCLOSURE OF INVENTION

According to the preferred embodiments, an apparatus measures residual stress in a sample under test by measuring the penetration of an indenter on a unprocessed sample under test, and after processing of the sample under test, measuring again the penetration of the indenter on the processed sample under test, and deriving from the two penetration measurements the residual stress in a sample under test. The apparatus and method of the preferred embodiments are especially useful in determining residual stress in a printed wiring board. In this manner a direct measurement of residual stress is possible without destroying the printed wiring board.

The foregoing and other features and advantages of the invention will be apparent from the following more particular description of preferred embodiments of the invention, as illustrated in the accompanying drawings.

BRIEF DESCRIPTION OF DRAWINGS

The preferred embodiments of the present invention will hereinafter be described in conjunction with the appended drawings, where like designations denote like elements, and.

BEST MODE FOR CARRYING OUT THE INVENTION

The preferred embodiments relate to the determination of residual stress in a sample under test. The apparatus and methods of the preferred embodiments may be used to determine residual stress in any isotropic material. In addition, the preferred embodiments are expressly well-suited to determining residual stress in a printed wiring board in a non-destructive manner.

The preferred embodiments comprise an apparatus similar in some ways to prior art Rockwell-type hardness testers. For this reason, the operation of a prior art hardness tester is described below with reference to FIGS. 1–4. The prior art hardness tester described herein is similar to the SwissRock 180 Universal Rockwell Hardness Tester available from Qualitest International Inc., 25 Valleywood Dr., Unit 21, Markham, Ontario L3R 5L9, Canada.

Figure 1:
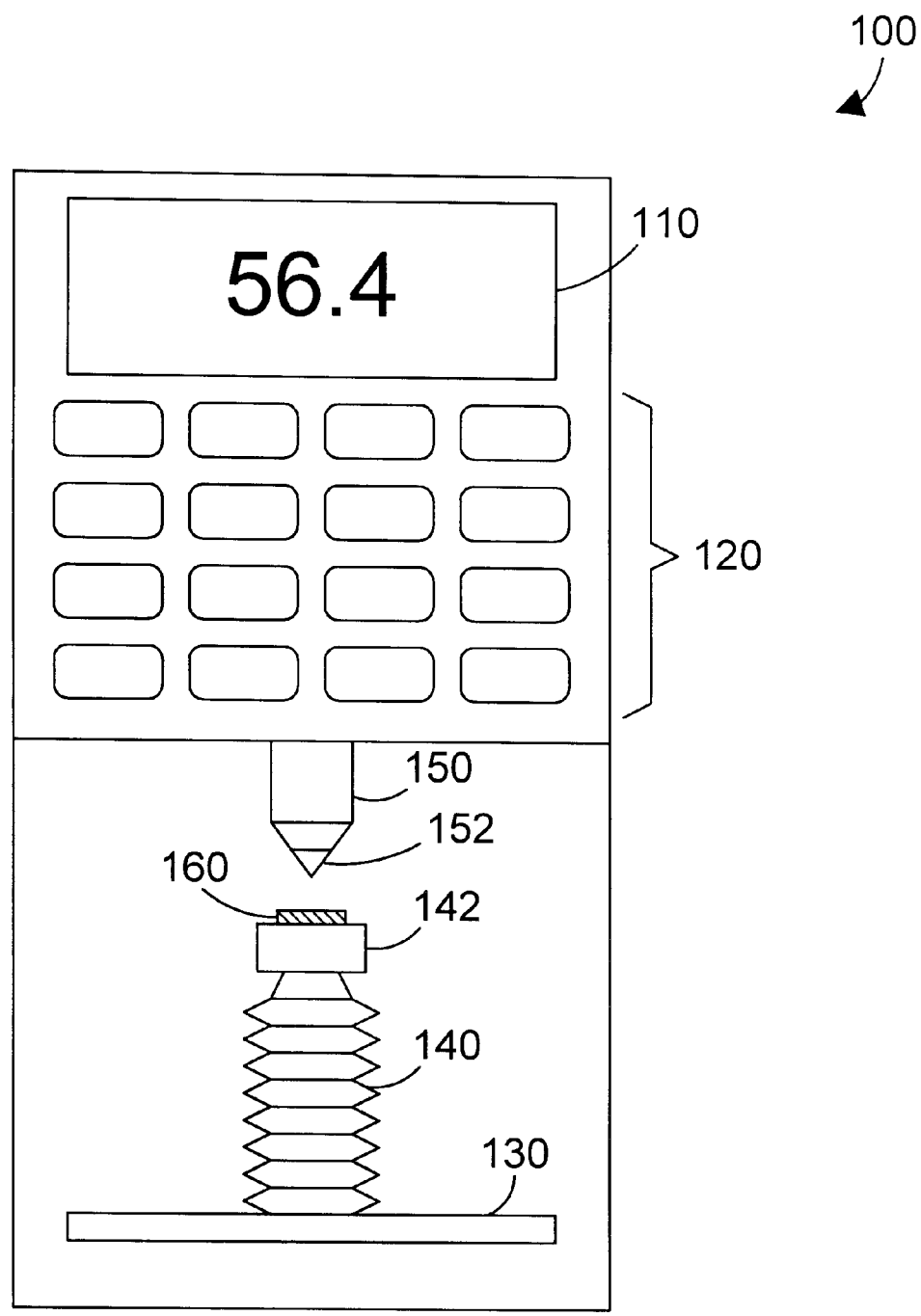
FIG. 1 is a front view of a prior art Rockwell-type hardness tester.

Referring to FIG. 1, a prior art Rockwell-type hardness tester 100 includes a display 110, a keypad 120, a base portion 130, an extendable plunger 140, and an indenter 150. The extendable plunger 140 includes a top portion 142 upon which is typically placed a sample under test 160. The indenter 150 includes a shaft coupled to an indenter tip 152. The indenter tip 152 in FIG. 1 is shown as a pointed tip. However, other tip configurations, such as a ball, are known in the art and are commonly used to test the hardness of various materials. To operate apparatus 100, the sample under test 160 is placed on the top portion 142 of plunger 140. The user then selects via the keypad 120 what force to apply to the sample under test 160, and presses one or more selected keys to cause the preselected test force to be applied to the sample under test 160. In the specific tester shown in FIG. 1, the plunger 140 extends upwardly to apply the preselected force to the sample under test 160 by pressing the sample under test 160 into the indenter 150. The apparatus 100 then determines the depth of penetration of the indenter tip 152 into the sample under test 160 when the preselected force is applied, and computes a Rockwell hardness number for the sample under test, which is displayed to the user on display 110. Note that prior art hardness testers such as 100 shown in FIG. 1 have been used primarily for measuring the Rockwell hardness of isotropic materials.

Figure 2:
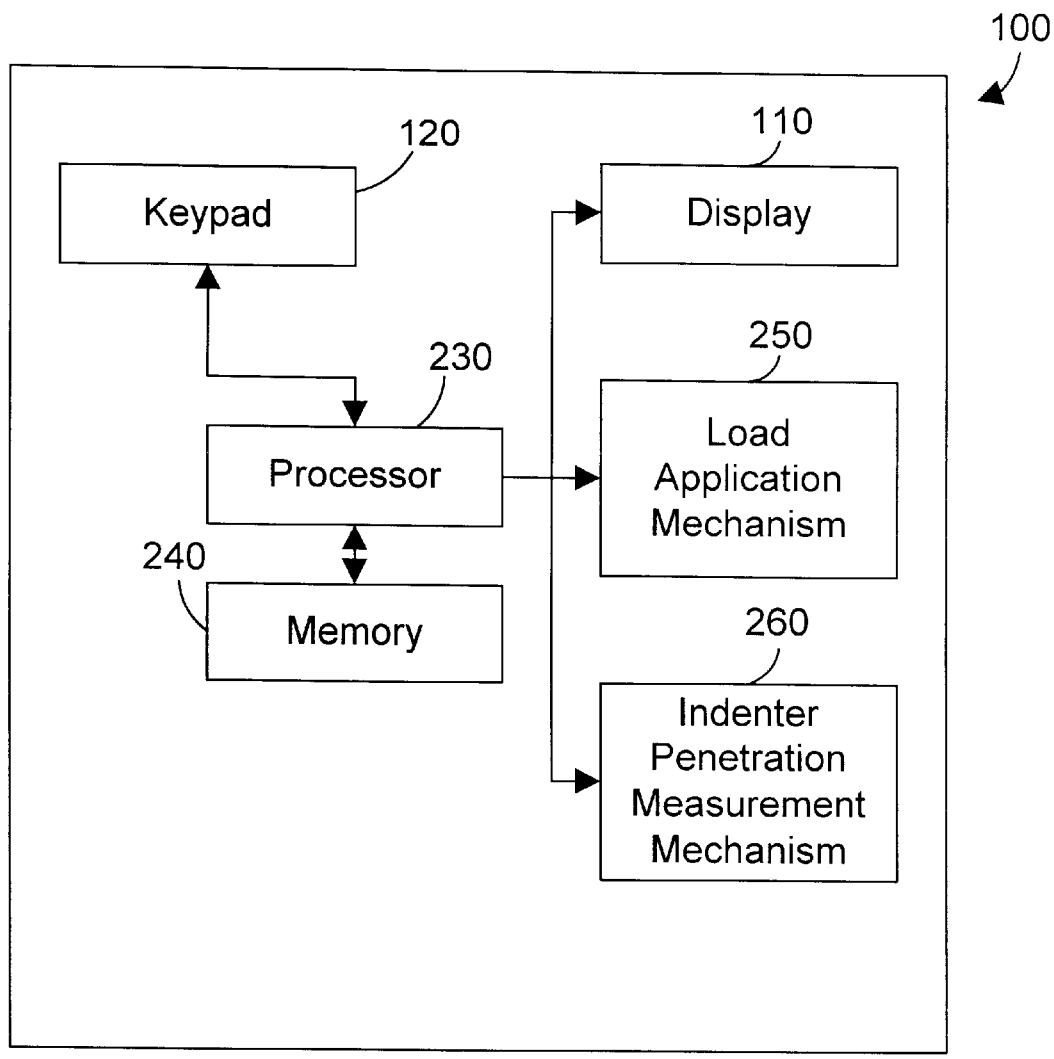
FIG. 2 is a block diagram of some of the components in the prior art hardness tester of FIG. 1.

Referring now to FIG. 2, an electrical block diagram of apparatus 100 shows the display 110 and keypad 120 that are shown in FIG. 1, but additionally shows other features that are not shown in FIG. 1. A processor 230 is included, and performs computation and control functions of apparatus 100. A memory 240 is coupled to the processor 230, and contains program code and data that may be accessed by processor 230. In addition to the display 110, processor 230 is also coupled to a load application mechanism 250 and an indenter penetration measurement mechanism 260. When a hardness test needs to be performed on a sample under test, the user presses appropriate keys on keypad 120 to instruct apparatus 100 to apply a preselected load to the sample under test. In response, the processor 230 instructs load application mechanism 250 to apply the preselected load to the sample under test. Once the preselected load has been applied for a predetermined period of time, the indenter penetration measurement mechanism 260 measures the penetration of the indenter tip into the sample under test, and communicates this penetration measurement to processor 230. Processor 230 then computes the Rockwell hardness from the load applied, the geometric configuration of the indenter tip, and the measured penetration of the indenter tip into the sample under test. The Rockwell hardness is then displayed on display 110. In this manner the Rockwell hardness of a sample under test may be quickly and conveniently determined.

Figure 3:
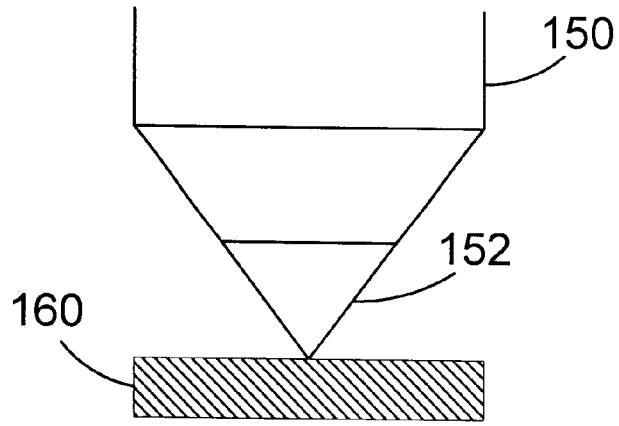
FIG. 3 is a close-up view the indenter of FIG. 1 before a force pushes the indenter into the sample under test.
Figure 4:
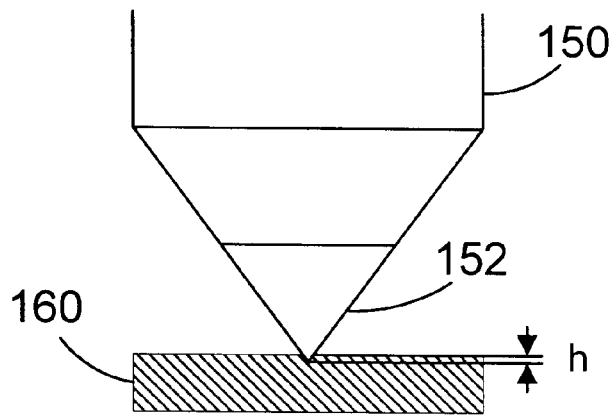
FIG. 4 is a close-up view of the indenter of FIG. 1 after a force pushes the indenter a distance h into the sample under test.

The penetration of the indenter tip into the sample under test is shown in more detail in FIGS. 3 and 4. FIG. 3 shows the indenter tip 152 in contact with the sample under test 160 with no load or a very small nominal load applied. FIG. 4 shows the indenter tip 152 in contact with the sample under test 160 with a preselected load applied. A penetration distance h in FIG. 4 is the penetration of the indenter tip 152 into the sample under test 160. Now the Rockwell hardness may be readily determined from the geometric configuration of the tip 152, the applied load, and the penetration distance h.

Figure 5:
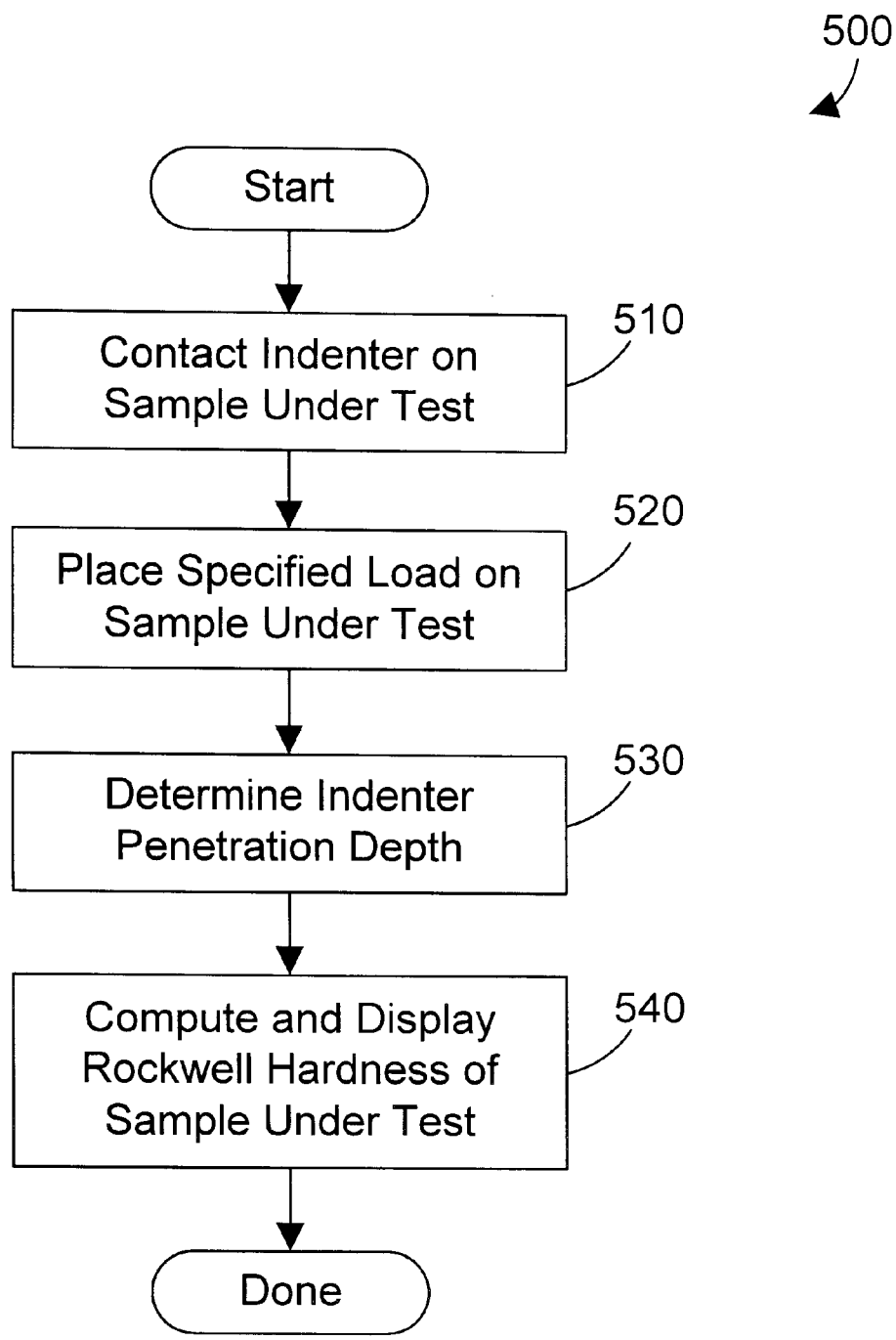
FIG. 5 is a flow diagram of a method for measuring the hardness of a sample under test using the prior art hardness tester of FIG. 1.

Referring now to FIG. 5, a prior art method 500 for measuring the Rockwell hardness of a sample under test first contacts the indenter on the sample under test (step 510). This is the situation for the indenter and sample under test in FIG. 3. Next, a specified load is placed on the sample under test (step 520). The penetration depth of the indenter into the sample under test is then determined (step 530). For example, in FIG. 3 the distance h of the penetration of the indenter tip 152 into the sample under test 160 is determined in step 530. Finally, the Rockwell hardness for the sample under test is computed and displayed (step 540) from the applied load, geometric configuration of the indenter tip, and the penetration distance h of the indenter tip into the sample under test. In the prior art, the formula for computing Rockwell hardness in step 540 is known as Kick's law, which is $P=Ch^2$, where P is the pressure applied by the preselected load, h is the penetration depth, and C is the curvature of the load versus penetration depth (which accounts for the geometric configuration of the indenter tip).

Figure 6:
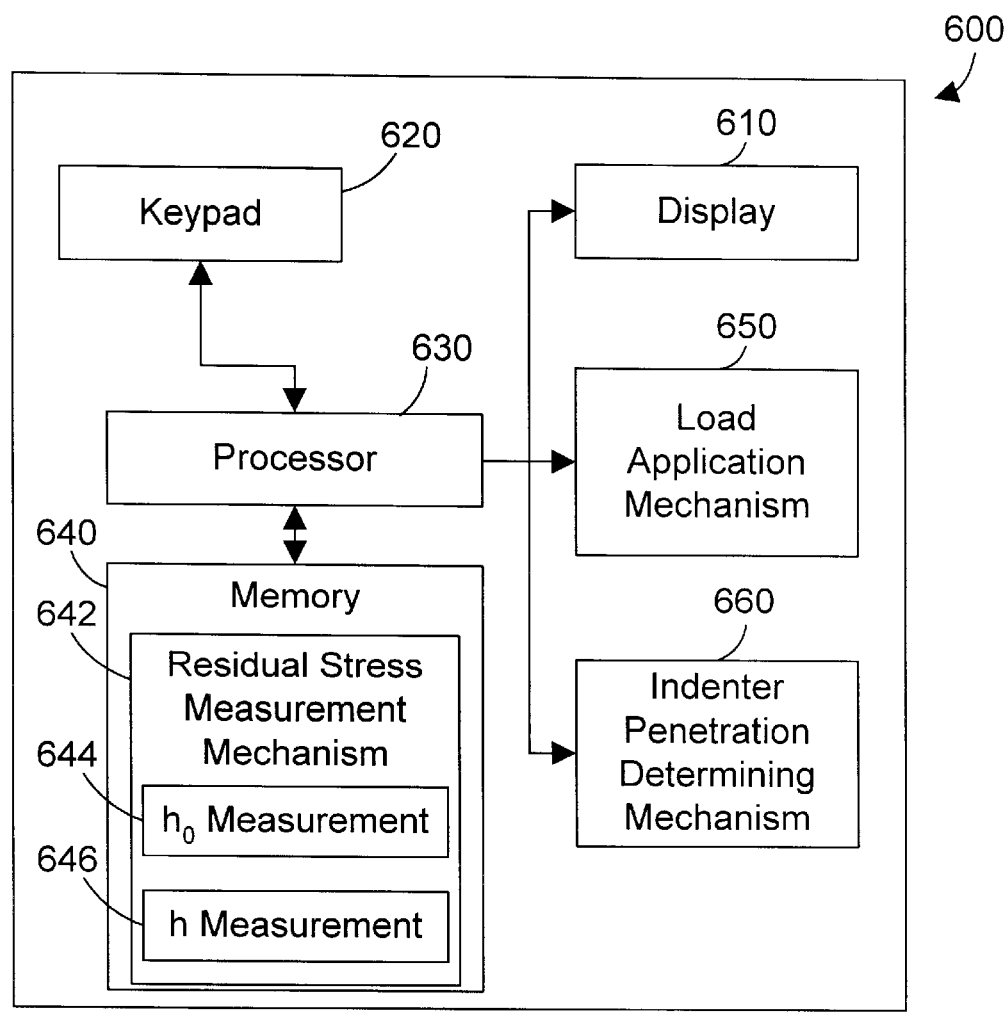
FIG. 6 is a block diagram of a residual stress tester in accordance with the preferred embodiments.
Figure 7:
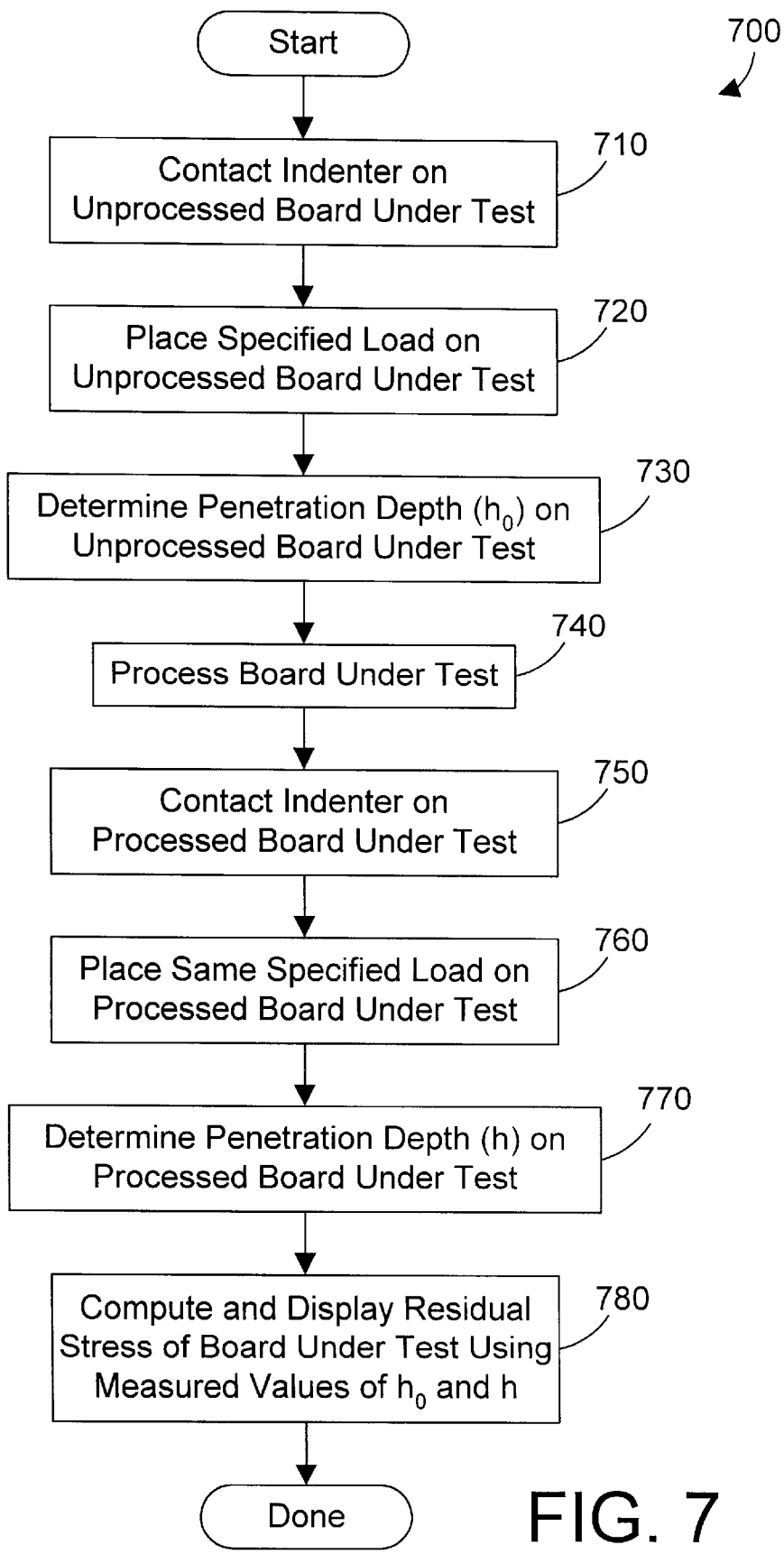
FIG. 7 is a flow diagram of a method in accordance with the preferred embodiments for measuring residual stress using the tester of FIG. 6.

The preferred embodiments are now discussed in reference to FIGS. 6 and 7. Referring to FIG. 6, an apparatus 600 in accordance with the preferred embodiments comprises a processor 630 coupled to a keypad 620, a memory 640, a display 610, a load application mechanism 650, and an indenter penetration determining mechanism 660. In the preferred embodiments, keypad 620 includes one or more keys to store a penetration value for a baseline sample under test, and one or more keys for computing and displaying residual stress. However, in the alternative, keypad 620 could also be similar to a prior art keypad (such as keypad 120 in FIGS. 1 and 2), where a user causes apparatus 600 to store the penetration value for a baseline sample under test, for a processed sample under test, and to compute and display residual stress by selecting one or more menu options that may be shown to a user on display 610.

In the preferred embodiments, apparatus 600 may be used to perform Rockwell-type hardness testing (as described above) in addition to determining residual stress in a sample under test. Display 610 is therefore used to display Rockwell hardness, and to also display residual stress when appropriate. Load application mechanism 650 is any suitable mechanism to apply a preselected load to the sample under test. One suitable method for applying a load to the sample under test uses dead weights coupled to a balance and lever system. Another suitable method for applying a load to the sample under test uses motorized load control where a motor applies dead weights to the sample under test. Of course, other mechanisms and methods may be used to apply a preselected load to the sample under test, including increasing force on the sample under test until strain gages on the indenter indicate the preselected load has been applied; increasing force on the sample under test until pressure in a hydraulic pressure indicates the preselected load has been applied, etc. Any and all mechanisms and methods for applying a force to a sample under test are included within the scope of the preferred embodiments, and the load application mechanism 650 of FIG. 6 is to be broadly construed to include all suitable mechanisms and methods.

Indenter penetration determining mechanism 660 is a mechanism that determines the depth (h) of penetration of the indenter tip 152 into the sample under test 160 (see FIG. 4). The depth of penetration can me measured or determined using any suitable method. One way to determine the depth of penetration uses an inductive frequency carrier. Another way is to measure the linear displacement of the sample under test or the indenter while the preselected force is applied to the sample under test. The preferred embodiments expressly extend to any and all mechanisms and methods for measuring or determining the penetration depth of the indenter tip into the sample under test.

Processor 630 is coupled to a memory 640. Within the memory 640 is a residual stress measurement mechanism 642. This mechanism allows applying a preselected load to the sample under test that is in contact with the indenter tip, and storing the penetration depth ($h_0$ 644) of the indenter tip into the baseline sample under test. This process is then repeated for a sample under test that has been processed, and the penetration depth (h 646) of the indenter tip into the processed sample under test is then measured. Once $h_0$ and h have been measured or otherwise determined and stored in memory 640, the residual stress and measurement mechanism 642 computes the residual stress in the sample under test using the equation:

$$h^2/h_0^2 = (1-(\text{residual stress})/p_{av})^{-1}$$

where h=penetration of the indenter into the sample under test after the sample under test is processed, $h_0$=penetration of the indenter into the sample under test before the sample under test is processed (the baseline sample), and $p_{av}$= average pressure (i.e., load) on the indenter that caused the penetration. Once the residual stress is computed, it is displayed on display 610. The apparatus of the preferred embodiments thus allow automatic determination of residual stress on a sample under test in a non-destructive manner.

While the apparatus is useful for determining residual stress in isotropic materials, it is also useful for determining residual stress in composite materials, such as fiberglass-epoxy multilayer printed wiring boards (PWBs). By determining residual stress using the apparatus and method of the preferred embodiments, PWBs may be tested to assure that they do not suffer excessive stress during the manufacturing processes that the PWB must undergo, including the placement of components on the PWB to form a printed wiring assembly (PWA), and the testing of the assembled PWA.

Referring to FIG. 7, a method 700 is used to measure residual stress in a sample under test. Because the preferred application is the measurement of residual stress in a printed wiring board, method 700 uses the term "board under test" rather than the broader term "sample under test." Note, however, that method 700 may be used to test any suitable material, including both isotropic and composite materials.

Method 700 begins by contacting the tip of the indenter to the unprocessed board under test with no load or a small nominal load (step 710). Next, a specified load is placed on the unprocessed board under test (step 720). This load will cause the indenter to penetrate the surface of the board under test. The depth of the penetration of the indenter tip into the board under test is then determined (step 730), and this value is stored in memory (see 644 in FIG. 6). Next, we assume in step 740 that the printed wiring board undergoes manufacturing processes, such as the assembly of components into the printed wiring board to form a printed wiring assembly, and various stress tests on the printed wiring assembly, including thermal cycles. Note that step 740 may include any suitable manufacturing process for the printed wiring board or printed wiring assembly that includes the printed wiring board.

Once the printed wiring board has been processed in step 740, it is then subjected to the same test that was performed before. The indenter tip is placed in contact with the processed board under test with no load or a small nominal load (step 750). Next, the same specified load that was used in step 720 is placed on the processed board under test (step 760). The penetration depth (h) of the indenter tip into the processed board under test is then determined (step 770) and stored (see 646 in FIG. 6). Finally, using the stored values of $h_0$ and h, the residual stress of the processed board under test is computed and displayed to the user (step 780). Note that method 700 uses the following formula in computing residual stress in step 780:

$$h^2/h_0^2 = (1-(\text{residual stress})/p_{av})^{-1}$$

where h=penetration of the indenter into the sample under test after the sample under test is processed, $h_0$=penetration of the indenter into the sample under test before the sample under test is processed (the baseline sample), and $p_{av}$= average pressure (i.e., load) on the indenter that caused the penetration.

Method 700 assumes that the same sample under test is tested before processing and after processing to determine its residual stress after processing. Note, however, that the method of the preferred embodiments can also be applied to different samples under test. Thus, an initial penetration depth $h_0$ may be determined for an unprocessed (baseline) sample under test, and penetration depth h could then be determined for the same load on a different processed sample under test. Of course, testing in this manner assumes that the samples under test have characteristics that are sufficiently similar that such testing between different samples under test will yield acceptable results. This assumption may be valid for tightly-controlled manufacturing processes that produce the samples under test, or when performed on samples under test from the same manufacturing lot. The preferred embodiments expressly extend to determining initial penetration of an indenter on a first sample under test, determining penetration of the indenter on a second sample under test, and computing residual stress on the second sample under test by assuming the initial penetration of the indenter for the second sample under test is the same as the initial penetration of the indenter for the first sample under test.

Test Results

The apparatus and method of the preferred embodiments were used to test various different samples under test for residual stress. Table 1 below shows the results of measuring residual stress in a piece of 17-7 PH stainless steel using a quarter bridge strain gage, and using the penetration depth method of the preferred embodiments.

TABLE 1

| Material | Measurement Technique | Test Condition | Residual Stress (psi) |
|---|---|---|---|
| 17-7 PH Stainless Steel | Quarter bridge strain gage | 500 lb. preload | 2325 |
| 17-7 PH Stainless Steel | Penetration Depth Method 700 | 500 lb. preload, 200 lb. applied load | 2543 |

We see from these empirical test results that the value for residual stress obtained by the penetration depth method of the preferred embodiments is within ten percent of the value obtained with the quarter bridge strain gage. This result illustrates that the method for testing for residual stress according to the preferred embodiments is a viable way of determining residual stress.

Tests were also performed on a fiberglass/epoxy/copper composite printed wiring board (PWB). The test results are shown below in Table 2.

TABLE 2

| Material | Measurement Technique | Test Condition | Residual Stress (psi) |
|---|---|---|---|
| 1.85 mm Backplane (18 layer, FR4/Cu) | Quarter bridge strain gage | 25 to 100 deg. C; 5 deg/min; 10 cycles | 3425 |
| 1.85 mm Backplane (18 layer, FR4/Cu) | Finite Element Model | 25 to 100 deg. C; 5 deg/min; 10 cycles | 4720 |
| 1.85 mm Backplane (18 layer, FR4/Cu) | Penetration Depth Method 700 | 25 to 100 deg. C; 5 deg/min; 10 cycles | 4565 |

The value for residual stress obtained by the penetration depth method of the preferred embodiments is within 25% of the value obtained using the quarter bridge strain gage, and within 4% of the value obtained using a finite element model, again indicating that the method for testing for residual stress according to the preferred embodiments is a viable way of measuring residual stress.

The preferred embodiments disclosed herein provide an apparatus and method for directly measuring residual stress on a sample under test by taking an unprocessed sample under test, applying a preselected load, determining the depth of penetration with the selected load, processing the sample under test, then applying the same preselected load, determining the depth of penetration with the preselected load, and computing the residual stress from the load, initial penetration (before processing), and penetration after processing. Note that this testing can be performed without destroying the printed wiring board, which is a very important feature in today's world of very sophisticated and expensive printed wiring boards.

While the preferred embodiments disclosed herein use a processor and memory to allow electronically computing residual stress using the formula above, it is also within the scope of the preferred embodiments to provide a mechanical method of directly indicating residual stress in a sample under test. For example, an existing Rockwell hardness tester that includes a mechanical dial could be modified to include a second mechanical dial for indicating residual stress. Thumb wheels or other mechanical means, such as levers or mechanical switches, could be provided that allow a user to enter either the depth of penetration or the Rockwell hardness for the baseline (unprocessed) sample under test. The thumb wheels, levers or switches could then alter the mechanical characteristics of the residual stress dial to allow directly reading from the dial the residual stress in a sample under test.

One skilled in the art will appreciate that many variations are possible within the scope of the present invention. Thus, while the invention has been particularly shown and described with reference to preferred embodiments thereof, it will be understood by those skilled in the art that these and other changes in form and details may be made therein without departing from the spirit and scope of the invention.

I claim:

1. A method for determining residual stress in a sample under test, the method comprising the steps of:
   (1) before the sample under test is processed, placing a specified load on an unprocessed sample under test that forces the unprocessed sample under test against an indenter, and determining the penetration of the indenter into the unprocessed sample under test;
   (2) processing the sample under test;
   (3) after the sample under test is processed, placing the specified load on the processed sample under test that forces the processed sample under test against the indenter, and determining the penetration of the indenter into the processed sample under test; and
   (4) determining the residual stress in the processed sample under test from the penetration of the indenter into the unprocessed sample under test and from the penetration of the indenter into the processed sample under test from the following formula:

$$h^2/h_0^2 = (1-(\text{residual stress})/p_{av})^{-1},$$

where
   h=penetration of the indenter into the sample under test after the sample under test is processed, $h_0$=penetration of the indenter into the sample under test before the sample under test is processed, and $p_{av}$=the specified load on the indenter.

2. The method of claim 1 wherein the sample under test comprises a printed wiring board that may receive a plurality of components.

3. The method of claim 1 wherein the processing of the sample under test comprises steps in assembling components into the printed wiring board to form a printed wiring assembly, and steps in testing the printed wiring assembly.

4. The method of claim 1 further comprising the step of displaying the residual stress to a user.

5. A method for determining residual stress in a printed wiring board, the method comprising the steps of:
   (1) after the printed wiring board is manufactured but before the printed wiring board is processed, performing the steps of:
      (1A) placing a specified load on an unprocessed printed wiring board that forces the unprocessed printed wiring board against an indenter; and
      (1B) determining the penetration of the indenter into the unprocessed printed wiring board;
   (2) processing the printed wiring board by performing the steps of:
      (2A) assembling a plurality of components into the printed wiring board to form a printed wiring assembly; and
      (2B) subjecting the printed wiring assembly to a plurality of thermal cycles;
   (3) after the printed wiring board is processed in step 2, performing the steps of:
      (3A) placing the specified load on the processed printed wiring board that forces the processed printed wiring board against the indenter; and
      (3B) determining the penetration of the indenter into the processed printed wiring board;
   (4) determining the residual stress in the processed printed wiring board from the formula:

$$h^2/h_0^2 = (1-(\text{residual stress})/p_{av})^{-1},$$

where
   h=penetration of the indenter into the printed wiring board after the printed wiring board is processed, $h_0$=penetration of the indenter into the printed wiring board before the printed wiring board is processed, and $p_{av}$=the specified load on the indenter; and
   (5) displaying the residual stress to a user.

6. A method for determining residual stress in a sample under test, the method comprising the steps of:
   (1) selecting a first of a plurality of items in a manufactured lot;

(2) before processing the first of the plurality of items, placing a specified load on the first of the plurality of items that forces the first of the plurality of items against an indenter, and determining the penetration of the indenter into the first of the plurality of items;

(3) processing a second of the plurality of items, the second of the plurality of items comprising the sample under test;

(4) after the second of the plurality of items is processed, placing the specified load on the second of the plurality of items that forces the second of the plurality of items against the indenter, and determining the penetration of the indenter into the second of the plurality of items; and (5) determining the residual stress in the second of the plurality of items from the penetration of the indenter into the first of the plurality of items and from the penetration of the indenter into the second of the plurality of items from the following formula:

$$h^2/h_0^2 = (1-(\text{residual stress})/p_{av})^{-1},$$

where h=penetration of the indenter into the second of the plurality of items after the second of the plurality of items is processed, $h_0$=penetration of the indenter into the first of the plurality of items before processing the first of the plurality of items, and $p_{av}$=the specified load on the indenter.

7. The method of claim 6 wherein the sample under test comprises a printed wiring board.

8. The method of claim 7 wherein the processing of the sample under test comprises steps in assembling components into the printed wiring board to form a printed wiring assembly, and steps in testing the printed wiring assembly.

9. The method of claim 6 further comprising the step of displaying the residual stress to a user.

* * * * *